(12) United States Patent
Vanden Berghe

(10) Patent No.: US 8,945,617 B2
(45) Date of Patent: Feb. 3, 2015

(54) EXTRUDATE AND METHODS OF USING SAID EXTRUDATE

(71) Applicant: Biominerals N.V., Destelbergen (BE)

(72) Inventor: Dirk André Richard Vanden Berghe, Laarne (BE)

(73) Assignee: Biominerals N.V., Destelbergen (BE)

( * ) Notice: Subject to any disclaimer, the term of this patent is extended or adjusted under 35 U.S.C. 154(b) by 0 days.

(21) Appl. No.: 14/281,258

(22) Filed: May 19, 2014

(65) Prior Publication Data

US 2014/0255493 A1 Sep. 11, 2014

Related U.S. Application Data

(62) Division of application No. 10/524,189, filed as application No. PCT/EP03/09009 on Aug. 12, 2003, now Pat. No. 8,771,757.

(30) Foreign Application Priority Data

Aug. 12, 2002 (EP) .................................... 02078336

(51) Int. Cl.
*A61K 9/58* (2006.01)
*A61K 9/14* (2006.01)
(Continued)

(52) U.S. Cl.
CPC .................. *A61K 33/00* (2013.01); *A23K 1/003* (2013.01); *A23K 1/1756* (2013.01); *A23L 1/0023* (2013.01);
(Continued)

(58) Field of Classification Search
CPC ....... A61K 33/00; A61K 47/186; A61K 9/14; A61K 8/25; A61K 9/1617; A61K 2800/92; A61K 9/5078; A61K 9/1694; A23K 1/003; A23K 1/1756; A23L 1/0023; A23L 1/0029; A23L 1/0305

USPC .......................................... 424/462, 489, 600
See application file for complete search history.

(56) References Cited

U.S. PATENT DOCUMENTS

| 5,922,360 A | 7/1999 | Bronder |
| 6,335,457 B1 | 1/2002 | Seguin et al. |
| 2006/0099276 A1 | 5/2006 | Vanden Berghe |

FOREIGN PATENT DOCUMENTS

| EP | 1110909 A1 | 6/2001 |
| JP | 9508349 T | 8/1997 |
| JP | 2001-158798 A | 6/2001 |

OTHER PUBLICATIONS

Decision to Grant a European Patent dated Mar. 19, 2009 issued in EP Application No. 03787792.5.
(Continued)

*Primary Examiner* — Aradhana Sasan
(74) *Attorney, Agent, or Firm* — Harness, Dickey & Pierce, P.L.C.

(57) ABSTRACT

The invention relates to a method for the preparation of a silicic acid comprising extrudate, comprising the steps of: i) forming of stabilized silicic acid, by hydrolyzing a silicon compound into orthosilicic acid and/or oligomers thereof in the presence of a stabilizing agent, which is a quaternary ammonium compound, or an amino-acid, or an amino acid source or combinations thereof; ii) mixing of the stabilized silicic acid with a carrier in an amount up to the loading capacity of the carrier for silicic acid; and iii) extruding the resulting mixture thereby forming the extrudate, to extrudates obtainable with the method, to an extrudate for use in the production of animal feed, feed supplement, human food and/or food supplement and of a pharmaceutical or cosmetic preparation, and for the treatment of infections, nails, hair, skin, teeth, collagen, connective tissue, bones, osteopenia, cell generation and degenerative (ageing) processes, and to a pharmaceutical composition comprising an extrudate.

18 Claims, 2 Drawing Sheets

(51) Int. Cl.
*A61K 33/00* (2006.01)
*A23K 1/00* (2006.01)
*A23K 1/175* (2006.01)
*A23L 1/00* (2006.01)
*A23L 1/03* (2006.01)
*A61K 8/25* (2006.01)
*A61K 9/16* (2006.01)
*A61Q 19/08* (2006.01)
*A61K 47/18* (2006.01)

(52) U.S. Cl.
CPC ............. *A23L 1/0029* (2013.01); *A23L 1/0305* (2013.01); *A61K 8/25* (2013.01); *A61K 9/1617* (2013.01); *A61Q 19/08* (2013.01); *A61K 9/14* (2013.01); *A61K 47/186* (2013.01); *A23V 2002/00* (2013.01); *A61K 2800/92* (2013.01)
USPC ............................ 424/462; 424/489; 424/600

(56) References Cited

OTHER PUBLICATIONS

Office Action dated Nov. 10, 2009 issued in U.S. Appl. No. 10/524,189.
Office Action dated Dec. 19, 2008 issued in U.S. Appl. No. 10/524,189.
Office Action dated Feb. 20, 2008 issued in U.S. Appl. No. 10/524,189.
Office Action dated Jan. 29, 2014 issued in U.S. Appl. No. 10/524,189.
Office Action dated Jun. 9, 2008 issued in U.S. Appl. No. 10/524,189.
International Preliminary Examination Report dated Nov. 2, 2004 issued in PCT Patent Application No. PCT/EP03/09009.
International Search Report dated Dec. 3, 2003 issued in PCT Patent Application No. PCT/EP03/09009.

EXTRUDATE AND METHODS OF USING SAID EXTRUDATE

CROSS REFERENCE TO RELATED APPLICATIONS

The present application is a divisional application of U.S. patent application Ser. No. 10/524,189 with a 371 (c) date of 15 Sep. 2005, which is a national stage entry of International Patent Application No. PCT/EP2003/009009 filed on 12 Aug. 2003, and which claims priority to European patent application EP 02078336.1 filed on 12 Aug. 2002. Each of the above-referenced patent applications is hereby incorporated by reference in its entirety.

FIELD

The present invention relates to a method for the preparation of a silicic acid comprising extrudate, to the said extrudate, to its particular uses and to a pharmaceutical composition which comprises the extrudate obtainable with the said method.

BACKGROUND

Silicon (Si) was reported to have an essential role in several organisms such as diatoms, Si accumulating plants, birds, and mammals. The formation of connective tissue components and other more specialized tissues such as bone and cartilage were shown to be dependent on the Si status. Dietary Si deficiency causes bone deformation, a thinner cortex, and a less calcified bone matrix (Carlisle, 1989, *Silicon in: Handbook of Nutritionally Essential Mineral Elements*, ed. B. L. Dell and R. A. Sunde, Marcel Dekker Inc., New York, pp. 603-618). Silicon deprivation in rats results in an altered bone mineral composition and decreased activity of bone specific phosphatase enzymes (Seaborn et al., 1994, *J Trace Elem Exp Med*, 7, 11). Therapeutic applications of silicon compounds were reported both in preclinical and clinical studies for a variety of diseases such as osteoporosis, atherosclerosis, neurodegenerative disorders, hypertension, aged skin, fragile hair and brittle nails, fungal infections, immunodeficiency, and connective tissue related diseases in general.

The bioavailability of silicon largely depends on its chemical form. Solid dietary silicon compounds have a low solubility and are poorly absorbed in the gastro-intestinal tract. Soluble silicon compounds found in beverages such as water and beer are readily absorbed and regarded as bioavailable sources of silicon. Orthosilicic acid which is the water soluble silicon compound present in these beverages is only stable at dilute concentrations. Concentrated complexes of orthosilicic acid were described with stabilizing agents such quaternary ammonium compounds and amino acids ("*Stabilized orthosilicic acid comprising preparation and biological preparation*", U.S. Pat. No. 5,922,360 and EP 0473922B1). These stabilized forms of orthosilicic acid were found to have a very high bioavailability compared to other silicon compounds in both animals and humans when administered as a liquid concentrate (Calomme et al., 1998, *Comparative bioavailability study of silicon supplements in healthy subjects*, Journal of Parenteral and Enteral Nutrition, 22, S12 and Van Dyck et al., 1999, *Bioavailability of silicon from foods and food supplements*, Fresenius Journal of Analytical Chemistry, 363, 541-544). A solid galenic from is preferred compared to liquid formulations when considering important issues such as dosing accuracy and compliance.

Several experiments were made in order to formulate a bioavailable, solid galenic formulation of silicic acid stabilized with quaternary ammonium compounds such as choline chloride, or an amino acid source. It is very difficult to make such a preparation since orthosilicic acid rapidly converts into non-bioavailable gels and precipitates. In fact, the addition of solid or semi-solid excipients without the addition of a non-toxic solvent agent result in polymerization or gel formation of orthosilicic acid into macromolecules, thereby decreasing the bioavailability of the final preparation. Direct filling of gelatine or methylcellulose capsules with a liquid matrix of choline stabilized silicic acid results in deformation and leaking of the capsule when incubated in stability tests. Stabilizing agents for orthosilicic acid such as choline chloride are extremely hygroscopic and attract water from the surrounding capsule which finally results in a deformed capsule.

SUMMARY

The present invention solves this problem and provides in a first aspect a method for the preparation of a bioavailable silicic acid comprising extrudate, comprising the steps of:
  i) forming of stabilized silicic acid, by hydrolyzing a silicon compound into orthosilicic acid and/or oligomers thereof in the presence of a stabilizing agent, which is a quaternary ammonium compound, or an amino-acid, or an amino acid source or combinations thereof; and
  ii) mixing of the stabilized silicic acid with a carrier in an amount up to the loading capacity of the carrier for silicic acid; and
  iii) extruding the resulting mixture thereby forming the extrudate.

A second aspect of the present invention provides the said extrudate for use in the production of animal feed or feed supplement, human food and food supplement and of a pharmaceutical or cosmetic preparation, and for the treatment of infections, nails, hair, skin, teeth, collagen, connective tissue, bones, osteopenia, cell generation and degenerative (ageing) processes.

A third aspect of the present invention relates to a pharmaceutical composition comprising the said extrudate.

DETAILED DESCRIPTION

In a preferred embodiment of the invention orthosilicic acid and oligomers thereof are used. Polymers of orthosilicic acid (OSA) are macromolecules formed from hundred or thousands of units called monomers (OSA) whereas oligomers are molecules of intermediate size—much larger than monomers (OSA) but less than macromolecules (Brinker C J et al, *Sol-Gel Science, The physics and Chemistry of Sol-gel processing*, Academic Press, Boston, p. 5). Generally oligomers of orthosilicic acid comprise up to about 100 orthosilicic acid units, such as 2-50, 2-40, or 2-30 orthosilicic acid units. As precursors of orthosilicic acid, hydrolysable silicon compounds are used such as silicon halogenides, silicon esters, silicates or alkylsilanol compounds such as ethoxysilanol. As a stabilizing agent a quaternary ammonium compound such as choline chloride, an amino acid such as proline, serine, lysine, arginine, glycine or combinations thereof or sources of amino acids such as polypeptides and protein hydrolysates can be used, such as porcine collagene, or gelatine. A particularly preferred embodiment of the invention is wherein the stabilized silicic acid and oligomers thereof comprises a silicon content of 2.5-3.5% by volume, a choline content 65-75% by weight and a water content of 15-25% by weight.

To provide a bioavailable solid form of the stabilized silicic acid, a carrier excipient, which can be used in extrusion technology, is added. Typical compounds that can be used as carriers for stabilized silicic acid are cellulose or a derivatives thereof such as microcrystalline cellulose, hydroxypropylcellulose, hydroxypropylmethylcellulose, carboxymethylcellulose, and cellulose gum. Other carriers or combinations with cellulose can be selected from sugars such as lactose, pectines and alginates, poly- and oligosaccharides such as malto-dextrine, glucans and derivatives thereof, starch and derivatives thereof, and natural and semi-synthetic fibers, proteins and protein hydrolysates.

In a preferred embodiment of the invention microcrystalline cellulose is used as a carrier for stabilized silicic acid. This results in a plastic mass which can be extruded and spheronized in pellets with a desired narrow particle size distribution. In the preferred embodiment the loading capacity for silicic acid is <50%, this means that a maximum of 50% by weight stabilized silicic acid is mixed with 50% by weight microcrystalline cellulose and an appropriate volume of water is added, sufficient to obtain the necessary granulate properties. A more preferred embodiment is to use 35% by weight choline stabilized silicic acid with 65% by weight microcrystalline cellulose.

EP 1 110 909 A1 discloses a silicic acid based preparation, which is prepared by using a solvent agent.

Figure 1:
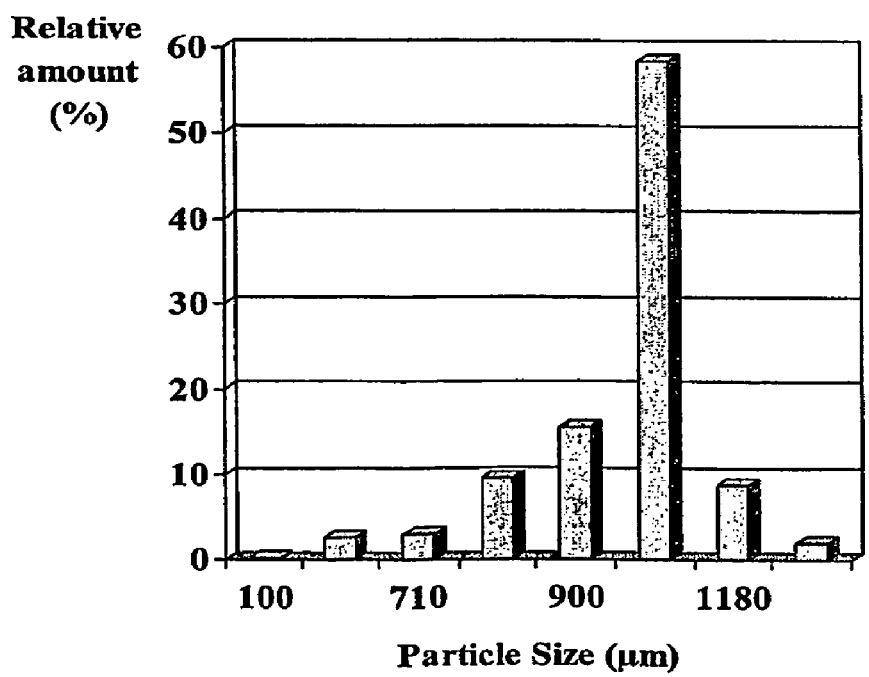
FIG. 1 is a graph representing particle size distribution of pellets obtained by extrusion-spheronization of choline stabilized silicic acid with microcrystalline cellulose as a carrier according to example embodiments.

The extruded strands are, in a preferred embodiment of the invention, transferred into a spheronizer where upon contact with a rotating friction plate, they are instantaneously broken down into particles. The obtained particles are dried to pellets by fluid bed drying or an another method using preferably a maximum temperature of 70° C. The final water content of the pellets after drying is preferably kept below 5% by weight. Higher water concentrations or drying temperatures above 70° C. are preferably avoided to limit polycondensabon of the stabilized silicic acid. Sieve analysis of the obtained pellets show that following the preferred method more than 90% of the pellets have a size between 800-1200 μm (see FIG. 1). The obtained pellets can be encapsulated, pressed to tablets, or used as a component in pharmaceutical preparations or in the manufacturing of food or animal feed.

The silicic acid extrudate according to the invention can be administered orally or in any other suitable fashion in the prevention and treatment of cardiovascular diseases such as atherosclerosis, musculoskeletal disorders such as osteopenia and tendinitis, chronic infections with destruction of the mucous membranes, forms of sinusitis and ulcers, infections such as dermatomycosis, neurological disorders, degenerative (ageing)-processes, immunodeficiency, and diseases affecting connective tissue and specialized tissue such as bone, teeth, nails, hair and skin.

EXAMPLES

Mentioned and further features and advantages of the present invention will be appreciated on the basis of the following drawings and examples. These examples are given for illustration purposes and are not intended to limit the scope of the invention.

Preparation Example A

Choline chloride is treated with dry hydrochloric acid. Silicon (IV) tetrachloride is added to the formed choline solution (ratio SiCl4 versus choline chloride: 1 mol per 1 to 5 mol). The resulting solution is hydrolyzed by adding water (ice/ice water) while cooling within a temperature range of −10° C. to −30° C. The solution is neutralized by adding sodium hydroxide and maintaining the temperature below 0° C. The final pH is between 1-1.5. Following a purification by active carbon, the precipitate is filtered off together with the active carbon. The water content is reduced by distillation under vacuum until a preparation is obtained containing 2.5-3.5% silicon by volume, 65-75% choline by weight, and 15-25% water by weight. 35% of the stabilized silicic acid solution (210 g) is slowly added to 65% microcrystalline cellulose (Avicel pH 101 or Vivapur type 101, 1390 g) under continuous mixing. Demineralized water is added (approximately 17% of the weight of Avicel) to obtain the desired granulate properties. The wet mass is extruded using a basket extruder (Caleva Model 10, Sturminster Newton, UK). The extrudate is spheronized at 750 rpm during 2 to 3 minutes (Caleva Model 120 sferonizer, Sturminster Newton, UK). The resulting spheres are dried until their water content is below 5% as determined by Karl-Fisher titration. Pellets exposed to the air are rapidly absorbing water as is demonstrated as in table 1. The silicon content of the pellets is 0.7-1.2% by weight.

Structure characterization using $^{29}$Si-NMR showed no signals between −30 and −70 ppm which is the spectral region for carbon (C) bonded silicon (Si). The spectrum showed resonances around −72, −82, −92, −102, and −1121 which are characteristic for $Q^0$, $Q^1$, $Q^2$, $Q^3$, and $Q^4$ species respectively. After incubation of 350 mg pellets in 1 ml buffer with pH 9.5 or artificial gastric fluid R (European Pharmacopoeia, 4$^{th}$ edition, p. 328), primarily signals of the species $Q^0$ (orthosilicic acid) are found in the $^{29}$Si-NMR spectra.

TABLE 1

Water content of pellets obtained from a extrudate of choline stabilized silicic acid.

| Time exposure to the air at room temperature (minutes) | Water content (%) |
|---|---|
| 0 | 4.91 |
| 15 | 5.15 |
| 180 | 7.95 |

Preparation Example B

Solution A:

Choline chloride is treated with dry hydrochloric acid. Silicon (IV) tetrachloride is added to the formed choline solution (ratio SiCl4 versus choline chloride: 1 mol per 1 to 5 mol).

Solution B:

A solution of porcine gelatine hydrolysate is prepared in water (1-5 g gelatine hydrolysate/100 ml water).

Solution A and B are mixed and immediately thereafter the resulting solution is hydrolysed by adding water (ice/ice water) while cooling within a temperature range of −10° C. to −30° C. The solution is neutralized by adding sodium hydroxide and maintaining the temperature below 0° C. The final pH is between 1-1.5. Following a purification by active carbon, the precipitate is filtered off together with the active carbon. The water content is reduced by distillation under vacuum. 35% of the stabilized silicic acid solution (210 g) is slowly added to 65% microcrystalline cellulose (Avicel pH 101 or Vivapur type 101, 1390 g) under continuous mixing. Demineralized water is added (approximately 17% of the weight of Avicel) to obtain the desired granulate properties. The wet mass is extruded using a basket extruder (Caleva Model 10, Sturminster Newton, UK). The extrudate is spheronized at 750 rpm during 2 to 3 minutes (Caleva Model 120 sferonizer, Sturminster Newton, UK). The resulting spheres are dried until their water content is below 5% as determined by Karl-Fisher titration. Pellets exposed to the air are rapidly absorbing water as is demonstrated as in table 1. The silicon content of the pellets is 0.2-1.2% by weight.

Preparation Example C

Choline chloride is treated with dry hydrochloric acid. Silicon (IV) tetrachloride is added to the formed choline solution (ratio SiCl4 versus choline chloride: 1 mol per 1 to 5 mol). The resulting solution is hydrolyzed by adding water (ice/ice water) while cooling within a temperature range of −10° C. to −30° C. The solution is neutralized by adding sodium hydroxide and maintaining the temperature below 0° C. The final pH is between 1-1.5. Following a purification by active carbon, the precipitate is filtered off together with the active carbon. A solution of collagen hydrolysate in water (5% w/v) is added in a ratio of 1:1. The water content is reduced by distillation under vacuum. 35% of the stabilized silicic acid solution (210 g) is slowly added to 65% microcrystalline cellulose (Avicel pH 101 or Vivapur type 101, 1390 g) under continuous mixing. Demineralized water is added (approximately 17% of the weight of Avicel) to obtain the desired granulate properties. The wet mass is extruded using a basket extruder (Caleva Model 10, Sturminster Newton, UK). The extrudate is spheronized at 750 rpm during 2 to 3 minutes (Caleva Model 120 sferonizer, Sturminster Newton, UK). The resulting spheres are dried until their water content is below 5% as determined by Karl-Fisher titration. Pellets exposed to the air are rapidly absorbing water as is demonstrated as in table 1. The silicon content of the pellets is 0.3-1.2% by weight.

Preparation Example D

Choline chloride is treated with dry hydrochloric acid. Silicon (IV) tetrachloride is added to the formed choline solution (ratio SiCl4 versus choline chloride: 1 mol per 1 to 5 mol). The resulting solution is hydrolyzed by adding water (ice/ice water) while cooling within a temperature range of −10° C. to −30° C. The solution is neutralized by adding sodium hydroxide and maintaining the temperature below 0° C. The final pH is between 1-1.5. Following a purification by active carbon, the precipitate is filtered off together with the active carbon. The water content is reduced by distillation under vacuum. 35% of the stabilized silicic acid solution (210 g) is slowly added to 50% microcrystalline cellulose (Avicel pH 101 or Vivapur type 101, 1390 g) and 15% dry collagen hydrolysate under continuous mixing. Demineralized water is added (approximately 17% of the weight of Avicel) to obtain the desired granulate properties. The wet mass is extruded using a basket extruder (Caleva Model 10, Sturminster Newton, UK). The extrudate is spheronized at 750 rpm during 2 to 3 minutes (Caleva Model 120 sferonizer, Sturminster Newton, UK). The resulting spheres are dried until their water content is below 5% as determined by Karl-Fisher titration. Pellets exposed to the air are rapidly absorbing water as is demonstrated as in table 1. The silicon content of the pellets is 0.3-1.2% by weight.

Formulation Example A

Pellets made according to the preparation example were encapsulated in vegecaps size o. The capsules were blistered in alu-alu blisters or packed in a high density polyethelene (HDPE) bottle and cover. The bottles were sealed and a silica gel sachet was enclosed. The packed pellets were incubated at 40° C. and 75% relative humidity for 6 months. After this incubation period the water content of pellets in both packaging materials was found to be comparable to the water content before incubation (see table 2).

TABLE 2

Water content of pellets obtained from a extrudate of choline stabilized silicic acid after incubation at 40° C. and 75% relative humidity

| Packing Material | Water content pellets (%) | | |
|---|---|---|---|
| | Prior to incubation | 3 months incubation | 6 months incubation |
| Alu-alu blister | 7.0 | 7.0 | 6.6 |
| HDPE bottle | 6.5 | 6.9 | 7.3 |

Formulation Example B

Pellets made according to the preparation example were encapsulated in vegecaps size o. The mean weight of pellets per capsule was 503 mg which was equal to a silicon dose per capsule of 4.5 mg.

Figure 2:
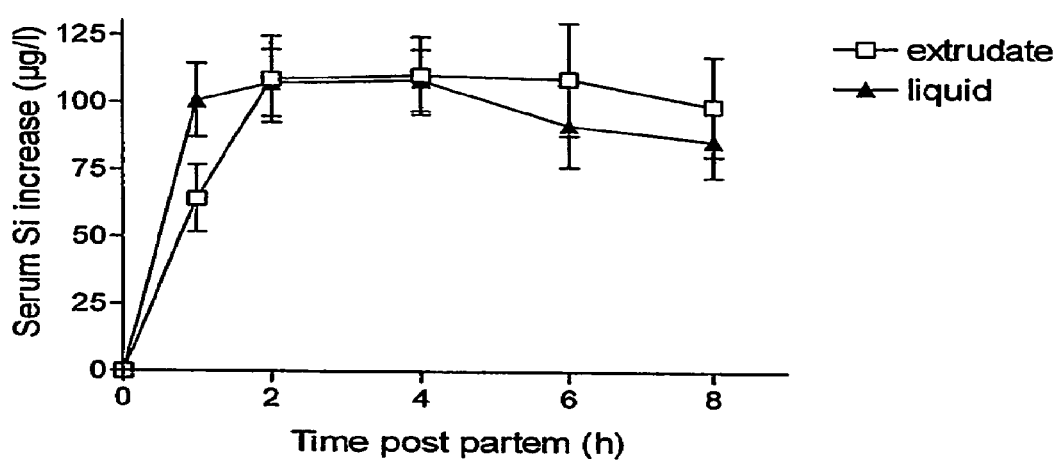
FIG. 2 is a graph representing increase in serum silicon concentration from the baseline level in 12 healthy subjects after supplementation of liquid stabilized orthosilicic acid ("liquid", 9 mg Si) and extruded stabilized silicic acid ("extrudate", 9 mg Si) according to example embodiments.
Figure 3:
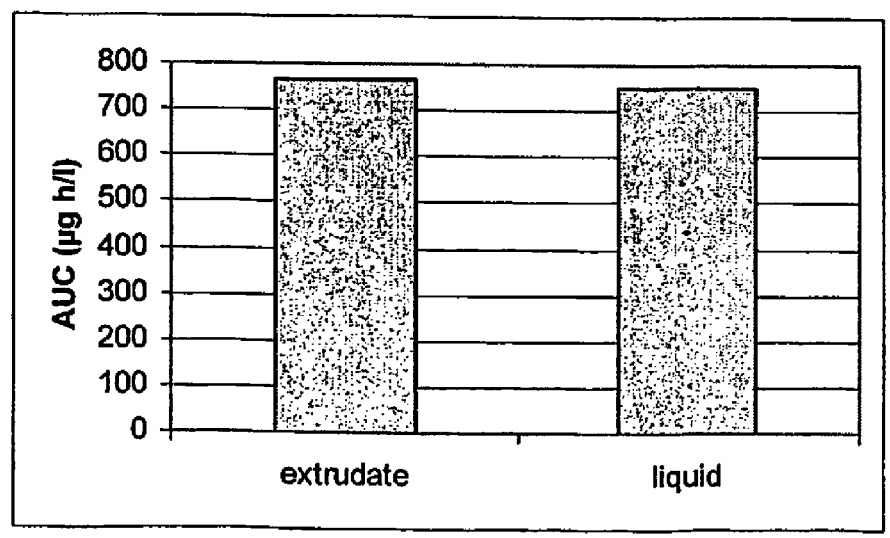
FIG. 3 is a graph representing total absorption of silicon in serum over a period of 0-8 hours after supplementation of liquid stabilized orthosilicic acid ("liquid", 9 mg Si) and extruded stabilized silicic acid ("extrudate", 9 mg Si) according to example embodiments.

Twelve healthy subjects (6 males, 6 females, age: 23-51 y) were included after informed, written consent. None had taken Si supplements within 3 months before the start of the study. Each fasting subject was administered in a cross-over protocol Si orally as follows: 9 mg of Si in the form of liquid choline stabilized orthosilicic acid (see FIG. 2 "liquid") and one week later 2 capsules of pelletized extrudate (see FIG. 2 "extrudate"). Blood samples were collected in Si free polypropylene tubes prior to supplementation and after 1, 2, 4, 6, and 8 hours post partem. Identical meals were consumed during the experiment at 2 and 6 hours after the silicon supplement was administered. The Si concentration was determined in serum with AAS (Zeeman Atomic Absorption Spectrometer, Perkin Elmer Corp., see FIG. 2). The area under the time curve was calculated using the linear trapezoidal rule and was used as a parameter of the total Si absorption ("bioavailability") within a period of 8 hours after the supplement was administrated (see FIG. 3).

The bioavailability of the extruded form of stabilized silicic acid was completely comparable to the liquid form and both forms had a similar kinetic profile in serum.

Formulation Example C

Pellets made according to the preparation example A, B, C or D were encapsulated in vegecaps size o. The mean weight of pellets per capsule was 324 mg which was equal to a silicon dose of 3 mg per capsule.

Four women with documented osteopenia in the hip (a T score equal or less than −1.5, see table 3) were supplemented during 12 months with the pelletized extrudate (1 capsule daily, 2 patients) or a placebo (control group, 1 capsule with 324 mg microcrystalline cellulose, 2 patients). All the patients were supplemented with 1000 mg calcium and 20 microgram cholecalciferol per day. Bone mineral density (BMD) of the hip was measured with DEXA at baseline (T0) and after 12 months supplementation (T12).

TABLE 3

Change in bone mineral density of the hip after 12 months supplementation with pelletized extrudate.

| | T score at baseline | Change in BMD (T12 versus T0, %) |
|---|---|---|
| Pelletized extrudate (3 mg Si/day) | | |
| Subject 1 | −2.02 | +0.72 |
| Subject 2 | −2.06 | +0.87 |
| Control Group (placebo) | | |
| Subject 3 | −1.87 | −1.40 |
| Subject 4 | −1.50 | −1.05 |

It was found that supplementation with the pelletized extrudate resulted in an increase of bone mineral density whereas in the placebo group BMD decreased. These results indicate that supplementation with the pelletized extrudate can be useful to prevent further bone loss in case.

The invention claimed is:

1. An extrudate obtained by a method comprising the steps of:
   i) forming a stabilized silicic acid by hydrolysing a silicon compound into orthosilicic acid and/or oligomers thereof in the presence of a stabilizing agent, which is a quaternary ammonium compound, or an amino-acid, or an amino acid source or combinations thereof;
   ii) mixing of the stabilized silicic acid with a carrier in an amount up to the loading capacity of the carrier for silicic acid; and
   iii) extruding the resulting mixture thereby forming the extrudate.

2. The extrudate of claim 1, wherein the extrudate comprises the stabilized silicic acid in a bioavailable form.

3. The extrudate of claim 1, wherein the stabilizing agent is choline.

4. The extrudate of claim 1, wherein the amino acid is proline, serine, lysine, arginine, glycine or combinations thereof.

5. The extrudate of claim 1, wherein the amino acid source is a polypeptide or a protein hydrolysate.

6. The extrudate of claim 1, wherein, prior to mixing with the carrier, the stabilized silicic acid comprises a silicon content of 2.5-3.5% by volume, a choline content of 65-75% by weight and a water content of 15-25% by weight.

7. The extrudate of claim 1, wherein the carrier is mixed with the stabilized silicic acid in a ratio of 65-50% and 35-50% respectively.

8. The extrudate of claim 1, wherein the carrier is selected from the group consisting of cellulose and derivatives of cellulose, sugars, pectines, alginates, poly- and oligosaccharides, starch and derivatives of starch, natural and semi-synthetic fibers, protein and protein hydrolysates and combinations thereof.

9. The extrudate of claim 8, wherein the carrier is cellulose or derivatives of cellulose.

10. The extrudate of claim 9, wherein the cellulose derivative is selected from the group consisting of microcrystalline cellulose, hydroxypropylcellulose, hydroxypropylmethylcellulose, carboxymethylcellulose and cellulose gum.

11. The extrudate of claim 9, wherein the carrier is microcrystalline cellulose and the loading capacity for the stabilized silicic acid is less than 50%.

12. The extrudate of claim 1, wherein the extrudate is spheronized into pellets.

13. The extrudate of claim 12, wherein at least 90% of the pellets, when dried, have a pellet size between about 800 to about 1200 microns.

14. The extrudate of claim 12, wherein the pellets are encapsulated.

15. The extrudate of claim 12, wherein the pellets are pressed into tablets.

16. The extrudate of claim 1 for use in the production of a feed and/or a food supplement for the treatment of a disease, an infection or a degenerative aging process in a subject in need thereof, and wherein the degenerative aging process affects connective tissue and specialized tissue.

17. The extrudate of claim 16, wherein the specialized tissue is selected from the group consisting of bone, teeth, nail, hair, skin and collagen.

18. The extrudate of claim 16, wherein the subject's bone mineral density increases.

* * * * *